United States Patent [19]

Paek

[11] 4,066,066
[45] Jan. 3, 1978

[54] ELECTRONIC PULSE FEELING DEVICE FOR PRACTICE OF DIAGNOSIS IN ORIENTAL MEDICINE

[76] Inventor: Hee Soo Paek, 8-29 2ga, Myunyoondong, Chongrogu, Seoul, South Korea

[21] Appl. No.: 627,356

[22] Filed: Oct. 30, 1975

[30] Foreign Application Priority Data

July 1, 1975 South Korea .............................. 1453

[51] Int. Cl.² .............................................. A61B 5/02
[52] U.S. Cl. ............................................... 128/2.05 P
[58] Field of Search ..................... 128/2.05 P, 2.05 R, 128/2 R, 2.1 C, 2.1 Z

[56] References Cited

U.S. PATENT DOCUMENTS

| 3,229,686 | 1/1966 | Edmark, Jr. | 128/2.05 R |
| 3,556,084 | 1/1971 | Budde | 128/2.05 P |
| 3,802,698 | 4/1974 | Burian | 128/2.05 P |
| 3,971,366 | 7/1976 | Motoyama | 128/2.1 Z |

FOREIGN PATENT DOCUMENTS

| 90,273 | 10/1967 | France | 128/2.05 P |
| 704,186 | 3/1941 | Germany | 128/2.05 P |

Primary Examiner—John D. Yasko
Assistant Examiner—L. Cohen
Attorney, Agent, or Firm—Fleit & Jacobson

[57] ABSTRACT

Electronic pulse feeling device for assisting the medical practitioner in making a diagnosis in oriental medicine by visually depicting wave forms of various different human vascular pulses. The waveforms which are produced may then be interpreted by a medical practitioner and compared to the descriptions of pulses in the old books of oriental medicine, thereby assisting the practitioner in learning the general location of the affliction and assisting the practitioner in reaching a diagnosis.

1 Claim, 9 Drawing Figures

FIG. 4
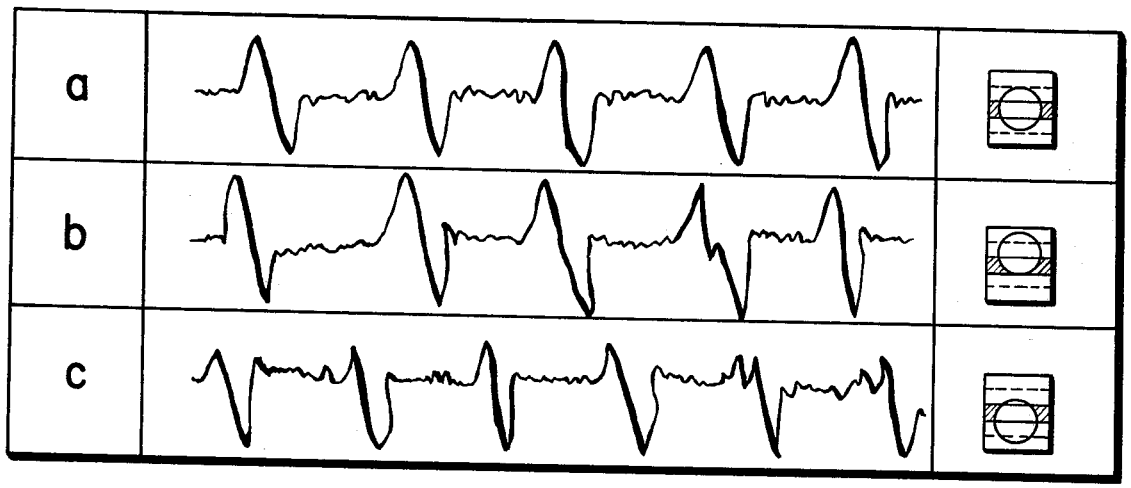
FIG. 5

ELECTRONIC PULSE FEELING DEVICE FOR PRACTICE OF DIAGNOSIS IN ORIENTAL MEDICINE

SUMMARY OF THE INVENTION

The present invention provides a method and apparatus for assisting a medical practitioner in sensing and categorizing various vascular pulses found at different locations in the human body. Multiple piezo-electric microphones are used to duplicate the kinetic sensations which have been in the past sensed by the human fingers. More specifically, microphones are located on the human body undergoing diagnosis along the radial artery at points corresponding to the chu, kwan, and chuck locations which have been described in old Chinese medical books. The microphones may be placed in contact with the predetermined locations by means of a suitable bandage or the like. In order to provide visual or graphic representations to the medical practitioner of the pulses which are sensed, the pulse signals from each microphone are fed to an amplifier section, the output of which is connected to a chart or strip recorder. A fourth microphone is employed and may be secured to the patients' arm by means of a sphygmomanometer cuff. This fourth microphone provides pulse rate or heart-beat frequency information. After amplification, this pulse information picked-up by microphone number 4 may be fed over a loud speaker so it may be heard simultaneously when viewing the graphs or strip-charts produced by the other three microphones. By providing a visual and/or aural representation of the vital signs of the blood vessels a better diagnosis using the ancient Chinese medicine methods may be made than if a diagnosis was made simply by use of the fingertips.

BRIEF DESCRIPTION OF DRAWING:

FIG. 4a. shows the wave form of a pulse which is strong in the positive energies and weak in the negative vital energies.

FIG. 4b. shows the wave forms of the pulses which are negatively strong and positively weak.

FIGS. 5a.b.c. show the wave forms of a normal pulse, a fatal swift pulse and a fatal slow pulse, respectively.

DETAILED DESCRIPTION

Figure 1:
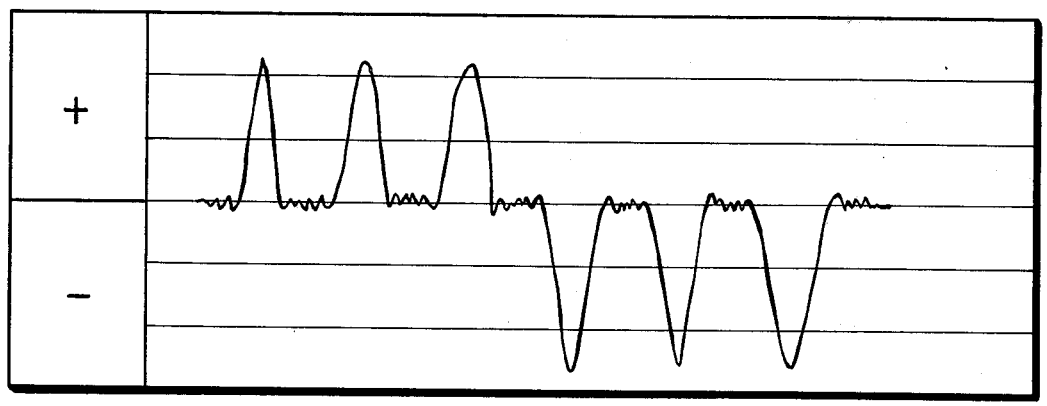
FIG. 1. shows a general form of pulse as depicted by this device, the pulse forms are considered to show the status of circulation of the blood and vital energies.

This invention is intended to provide apparatus which may be used by the practitioner of oriental medicine as an aid to more easily make a diagnosis of illness in accordance with the theories of oriental medicine.

In the practice of modern medicine, many scientific devices such as audiophone, sphymomanometer, X-ray, and cardiograph are being used.

But in the practice of oriental medicine, none of such devices is used, and diagnosis is being done solely by the feeling of pulses by the medical practitioner's fingers; that is, diagnosis depends solely upon the sensitivity of human fingers.

This uncertain and subjective method is very likely to produce a wrong diagnosis and consequent mistreatment of diseases.

Moreover, instruction of theories of pulse feeling has been so difficult because of the total lack of any visual or tangible means of representing the pulses. Only experts with long years of experience could do fairly reliable diagnosis.

This invention is to achieve a major improvement in the practice of oriental medicine by visually depicting wave forms of pulses which correspond to the descriptions of pulses in the old books of oriental medicine, Nae-Kyung and Nan-Kyung and thus enabling a practitioner of oriental medicine to make a reliable diagnosis.

This invention makes use of piezo electricity.

The pressure variations in the wave forms of pulses are converted into electric impulses at the points for pulse feeling.

These, in turn, are amplified and displayed on the display tube and count display.

This device records the display of wave forms and tells the frequency of pulse too.

This device has successfully recorded all the types of pulses which are described in the Nae-Kyung and Nan-Kyung, such as the so-called nine different types of pulses at three pulse points.

Diagnosis of illness in accordance with the oriental pulse theories can now be done systematically and scientifically.

Required knowledge for use of this device in the diagnosis is a simple one.

It is only necessary to fully understand and memorize the forms and characteristics of six basic types of pulses: a sharp, a sluggish, a large, a small, a smooth and a rough pulse. So, the economy is also achieved in the study of oriental medicine with reduction of time requirement.

To more effectively appreciate the functions of this device it seems necessary to undestand the word "Chon-goo" which is the main pulse feeling point. "Chon-goo" is the point just below the end of process of the bone "radius" on the wrist.

Vital energies are considered to converge at "Chon-goo" and the pulses felt at this point are supposed to indicate all the status of the circulation of vital energies.

Two more pulse feeling points are added to "Chon-goo": one called "Kwan" and the other "Chuk". At these three points, pulses are felt and classified into three types: floating, average and sunk. A floating pulse is one that can easily be felt by just a slight touching and a sunk one is that which is felt only with a considerable pressure to reach the bone, and the average pulse is one that goes between the above two.

In oriental medicine "Chon-goo" is compared to the heaven, and the pulses at that point are used in the diagnosis of illness at points on the body from the head to the breast. Kwan, compared to the human, is used in the diagnosis of illness on the part form the midriff to the navel; and Chuk, compared to the earth, is used in the diagnosis of illness on the part from the navel to the end of feet.

The pulse theores are based on the so called Oh-Heng theory (the pentagonal movement theory, which is very abstract and difficult to understand.

Consequently, pulse theories are also very abstract and very difficult to understand but now aided by this device, one may be facilitated in the understanding of them.

By feeling pulse at Chon-goo, the conditions of the positive and the negative vital energies of a subject can be determined.

In FIG. 1. the parts of the pulses marked plus are the positive pulses which are produced during the time of exhaling and are related to the vital energies of the lungs and the heart.

The parts indicated in the negative region are the negative pulse and, produced during inhaling are related to the vital energies of the kidneys and the bladder.

The pulses of the spleen are supposed to appear between the times for exhaling and inhaling pulses of the lungs and that of heart however, they don't appear in the same floating forms, although they belong to same positive family.

The pulses of the heart are slightly floating, large and dispersed ones; while that of the lungs feel slightly floating, short and pulsating.

Pulses of the kidneys and of the liver also don't show the same sunk forms although they belong to the same negative family; the former feeling soft and vigorous upon little reduction of the finger pressure; and the latter feeling solid and long.

The pulses of the spleen are neither floating nor sunk, and are intermediary in nature.

The fourth article of Nan-Kyung also relate to the feeling of pulses at Chon-goo for the determination of the status of vital energies, negative and positive.

Figure 2A:
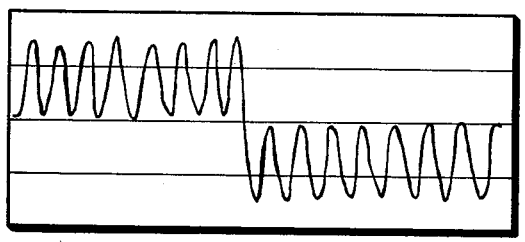
FIG. 2a. shows a wave form of swift pulse.
Figure 2B:
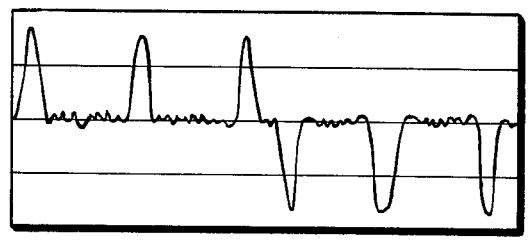
FIG. 2b. shows a wave form of slow pulse.

When the pulses are swift as shown in the FIG. 2a. diseases are supposed to belong to the positive organs, and when the the pulses sluggish as shown in the FIG. 2b. diseases are on the negative organs.

The heart, the lungs, the kidneys, the liver and spleen are characterized as negative organs.

As mentioned earlier there are six basic types of pulses: a swift, a sluggish, a large, a small, a smooth and a rough pulses.

Figure 3:
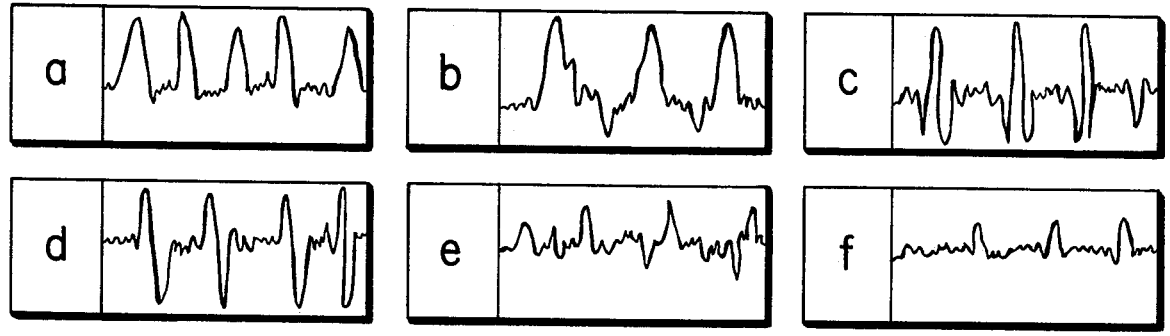
FIG. 3. shows six basic forms of pulses: a. swift pulse; b. sluggish pulse; c. large pulse; d. small pulse; e. smooth pulse; f. rough pulse.

Swift pulses (also called floating or tense pulses) shown on FIG. 3a. are tense in character and related illness is accompanied by chill.

Sluggish pulses (also called sunk pulses) shown on FIG. 3b. are lazy in feeling and related to a diseases with high temperature.

Large pulse (also called long pulses) shown on FIG. 3c. are for a person abundant in vigor.

Small pulses (also called slender or short pulses) shown on FIG. 3d indicate deterioration of stamina and vital energies.

Smooth pulses shown on FIG. 3e. indicate existence of heat developed in the body and a status of strong positivity and weak negativity or viceversa.

Rough pulses shown on FIG. 3f. indicate a condition of stagnation of vital energies or blood in the course of circulation.

This is also a status of deterioration in blood functions.

The knowledge of the six basic pulse types and that of the pentagonal movement theory are vital in the reading of pulse graphs. Each of the six basic types can further be subdivided into two kinds: a severe and a slight; thereby making up twelve types.

These twelve types are again classified into two categories: a sunk and a floating; thus making up twenty-four types.

These twenty-four types are to be taken at six different points on both wrists thus 144 type of pulses can be imagined. (12 × 6) True, those numerous pulse types can not be distinguished with the sense of fingers.

This device makes it possible to discriminate all those numerous forms of pulses.

FIG. 4a. shows a pulse form, depicted by this device, of the so-called status of strong positivity and weak negativity in which the positive organs function strongly, while the negative organs are not functioning adequately.

When the pulses appear above the datum line in the graph, the condition of body is in the status of strong positivity and weak negativity.

The status of strong negativity and weak positivity is depicted below the datum line, as shown on FIG. 4b.

The former is also a floating pulse, while the latter is a sunk pulse.

All those different pulse forms can clearly and easily be depicted by a rather simple method of manipulation of this device.

EXAMPLE 1 METHOD OF MANIPULATION

Figure 6:
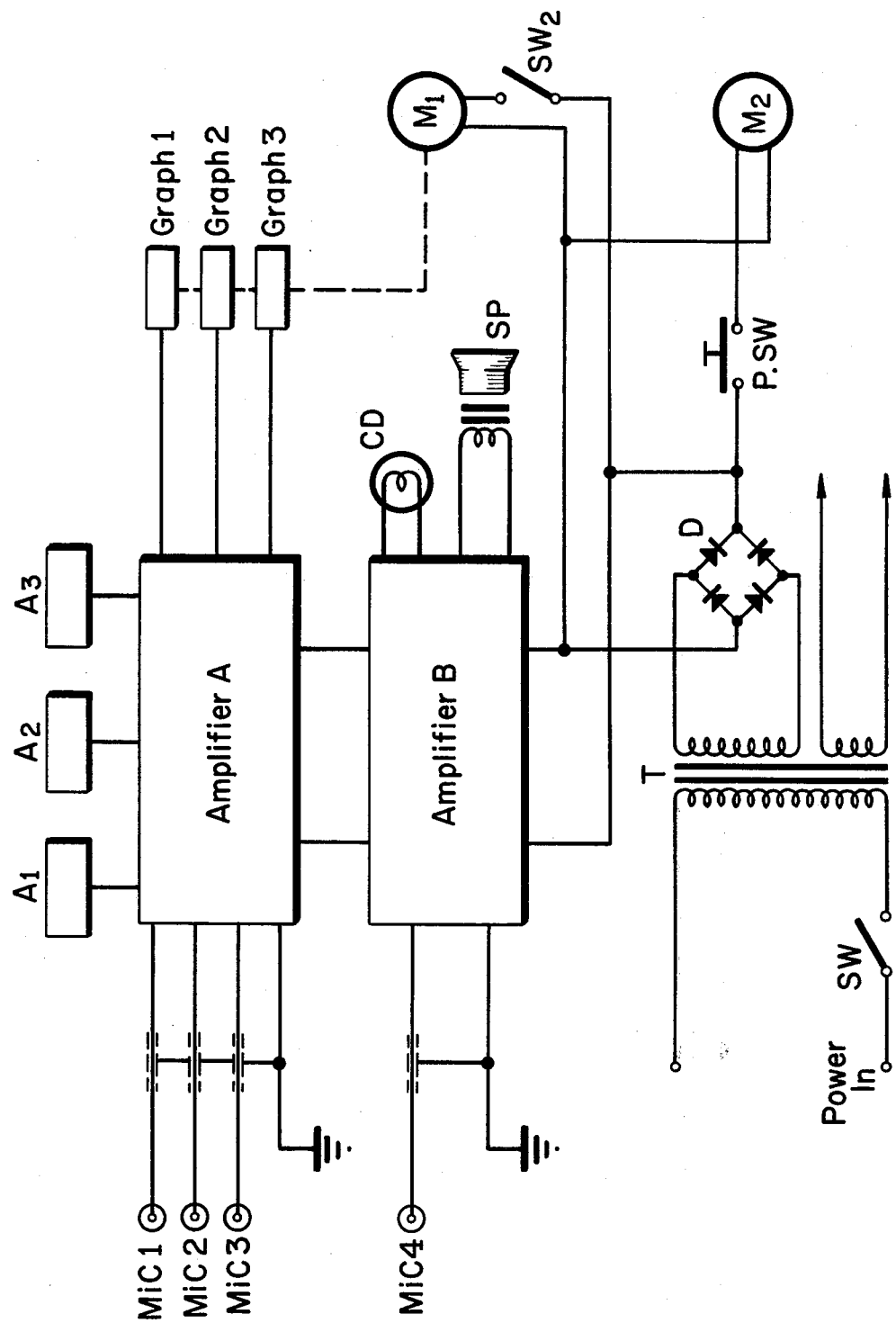
FIG. 6 is a general block diagram of the electronic device hereby applied for a patent.

Turning on the switch shown on FIG. 6, this device starts to function. Rectified electricity motivates the amplifiers, Amp A and Amp B shown on FIG. 6.

Figure 7:
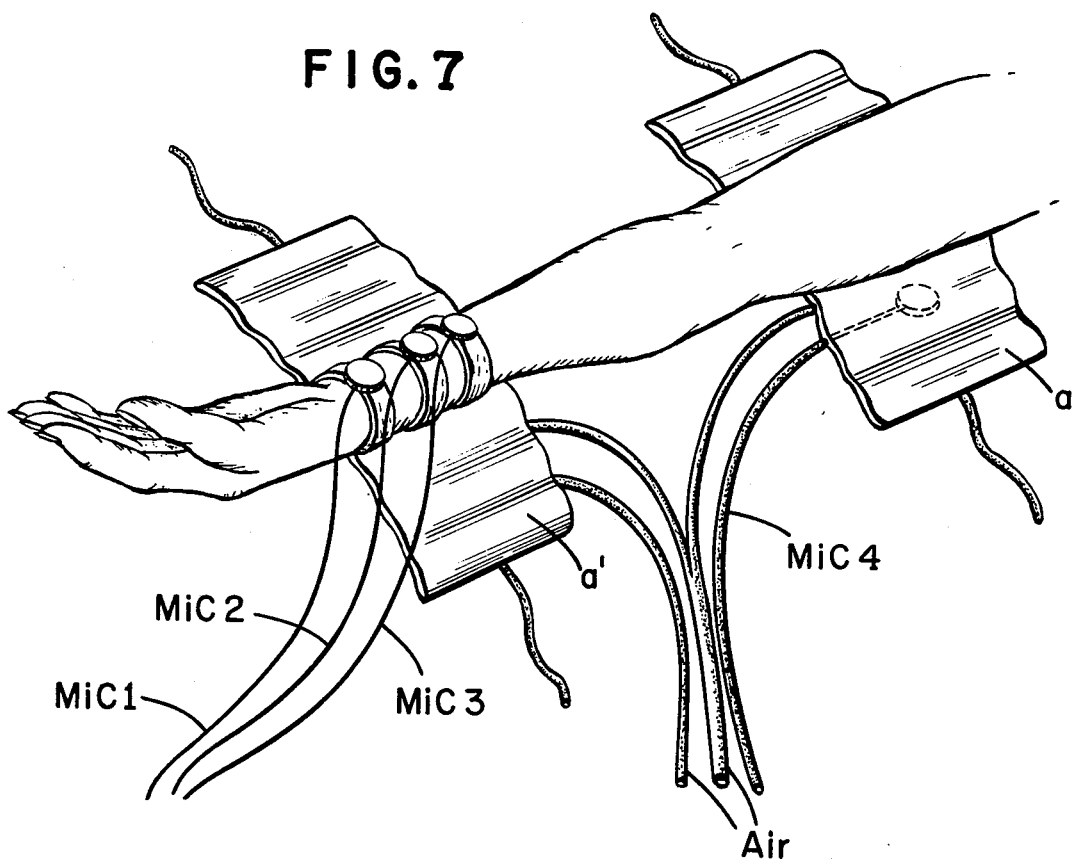
FIG. 7 shows the locations of pulses which are felt by this device making use of piezo electricity.

Crystal microphones are placed on the pulse points of the wrist as shown on FIG. 7, by means of a suitable bandage.

Another microphone (mic 4) on bandage a of FIG. 7 is also placed on the elbow. This mic. 4 is connected to a sphygomanometer (not shown on the diagram).

Turning on the push switch (P.SW), the motor ($m_2$) starts to run an air compressor (not shown) which inflates the bandages $a'$ and $a$ of FIG. 7.

The microphone 4 (mic. 4) supplies the information concerning the frequency of pulse at the high blood pressure.

This information is then amplified by an auxiliary amplifier. (Amp. B).

This amplified information then is sent to the speaker (SP) and to the display tube where a numeral is read to indicate the frequency of pulse.

The pulse forms detected by the microphones (mic. 1, mic. 2, mic. 3) are amplified at amplifier A(Amp. A of FIG. 6), and then are sent to ammeters ($A, A_2, A_3$) an also to graphic recorder(graph 1, graph 2 and graph 3 of FIG. 6).

The switch 2(SW 2) runs the motor 1($m_1$) which moves the rolls of recording paper.

The above process mentioned in this illustration is repeated at three different blood pressures, high, low and average, and at both wrists, and consequently eighteen different pulse graphs are produced for one subject.

EXAMPLE 2 WAVE FORMS OF A NORMAL, A FATAL SWIFT AND A FATAL-SLOW PULSES

FIG. 5a, is a normal pulse; FIG. 5b, a fatal-swift pulse; and FIG. 5a, a fatal-slow pulse.

In discussing the frequency of pulses, if pulsation takes place four times per a cycle of breathing, then this pulse is called a normal one if pulsation takes place six times for one cycle of breathing, then this is called abnormal.

With eight pulsations the pulse is called a vacancy of vital energies, with ten pulsations the pulse is called a dying pulse.

When twelve pulsations occur in one cycle of breathing the pulse is called a dead one, meaning pulse is already dead.

This dead pulse is also called a fatal-swift pulse which is again a condition of extreme danger in the process of disease.

A fatal-slow pulse is one in which only one pulsation takes place during the time period in which four cycles of breathing are done for healthy persons. At this fatal-slow pulse, all the positive vital energies are said to be exhausted.

The fatal-swift pulse is considered to occur when the disease has proceeded from the kidney and then up to the liver, to the spleen and finally to the heart, while the fatal slow pulse is considered to occur when the disease has proceeded in a reverse order from the above.

The FIGS. 5a, 5b, and 5c, serve as criteria for pulse form reading.

EXAMPLE 3 DETECTION OF FAILING ORGANS

To discover whether a certain one of the organs of a body is functioning properly or not it is only necessary to read the count display:

If in the count display, one pulse fails to appear in fifty continuous pulsations, then the kidneys are not functioning properly.

It is believed that the negative organs, the liver and the kidneys, are associated with inhaling breath and the positive organs, the heart and the lungs, are associated with exhaling breath, and this breathing motivates the circulation of the vital energies along the twelve meridians in the body, and this circulation converges at Chon-goo.

The failure of a pulse per every fifty pulsations is due to inadequate circulation of the vital energies. This inadequacy causes the failure of vital energies to reach the kidneys.

Thus, the kidneys, excluded from the circulation of vital energies, become deteriorated and exhausted. The eleventh article of Nan-Kung also discussed these theories.

EXAMPLE 4 DETECTION OF OTHER IMPORTANT PULSE FORMS: A CONCEALED, A OVERWHELMING AND A SUPERIMPASING PULSES

To do this, only extra standard wave forms are necessary.

According to the theories of oriental medicine, Chon-goo is supposed to show the positive forms of pulses and chuk to show negative pulses but sometime, stronger opposite forms of pulse are present and original forms of pulses become hidden under the stronger pulses thus appearing only very weakly. These hidden weak pulses are called "concealed pulses".

The invading pulse forms appearing strong, are called "superimposing pulses".

For example, at chuk, the negative forms of pulses are supposed to appear, in a sunk, rough and short form (according to the theories of oriental medicine).

Figure 8:
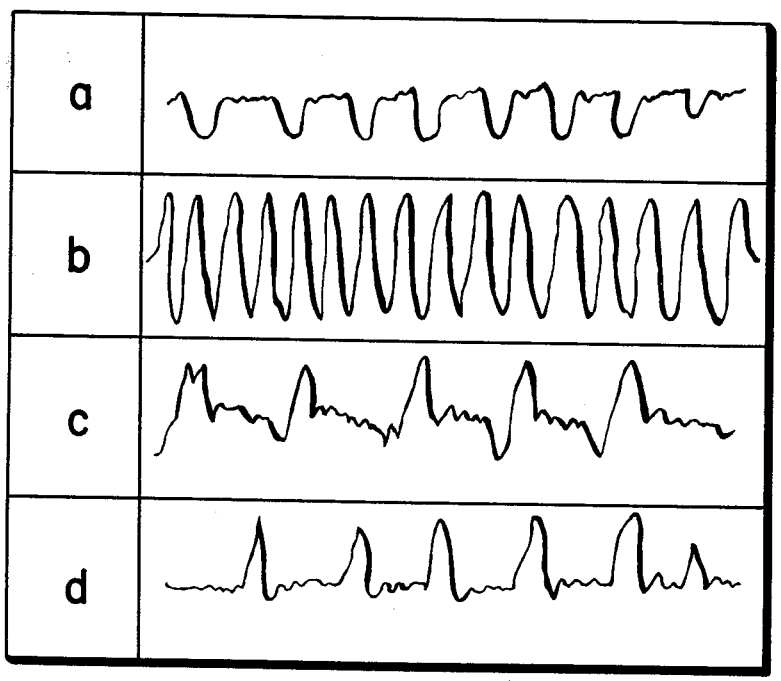
FIGS. 8a.b.c.d. show the wave forms of a negative-overwhelming pulse, a negative-concealed pulse, a positive-overwhelming pulse and a positive-concealed pulse, respectively, as described in the 20th article of Nan-Kyung.

But, when invaded by a pulse becomes concealed under the invading superimposing pulse, as shown on FIG. 8b.

Similarly, if a strong negative pulse invades in the Chon-goo, the original positive pulses hidden under the invader.

In this case the invader is "negative superimposing pulse" and the original one is "positive concealed pulse", as shown on FIG. 8d. The characteristics of positive pulses are of floating smooth, and long forms.

When the superimposing pulse is so strong that no concealed pulse appears, the pulse is said to be "overwhelming".-(FIG. 8a and c)

When a overwhelming pulse occurs, all the pulse forms felt at Chon-goo and at chuk are in the same category, either a positive or a negative.

Thus, in case of a positive-overwhelming pulse all the pulses taken at Chon-goo and Chuk are of the positive form, and in case of negative-overwhelming, all the pulses taken are of the negative form.

In the case of negative-overwhelming the disease related is a mental disturbance and in the case of the positive overwhelming, the related disease is epilepsy.

The positive overwhelming pulse also occurs in case of exhaustion of the positive vital energies, the related disease being mental disturbance.

The negative overwhelming pulse also occurs in case of exhaustion of the negative vital energies, the related disease being deterioration of sight. FIG. 8a,b,c,d, serve as criteria for detection of those wave forms mentioned in this illustration.

The illustrations so far given are only part of the functions of this invention while many other useful uses can be made.

What is claim is:

1. Pulse feeling apparatus for use in aiding a medical practitioner in making a diagnosis in the practice of oriental medicine, comprising in combination:

four microphone means each producing electrical signals corresponding to human vascular pulses;

means for restricting blood flow and for positioning a first of said microphone means inside the arm at the elbow whereby said first of said microphone means produces a first electrical signal representing the frequency of the vascular pulse at the location of said restricted blood flow, means for positioning a second, third, and fourth of said microphone means on the arm at three preselected locations, amplifier means connected to receive said electrical signals from said microphone means for producing amplified signals therefrom, graphical representation means connected to be driven by said amplified signals from said amplifier means corresponding to said second, third, and fourth microphone means electrical signals, and count display means connected to be driven by said amplified signal from said amplifier means corresponding to the signal produced by said first microphone means representing the pulse rate whereby the pulse rate is communicated to said medical practitioner.

* * * * *